United States Patent
Batzer et al.

(10) Patent No.: US 9,955,923 B2
(45) Date of Patent: May 1, 2018

(54) ARRANGEMENT COMPRISING A PATIENT SUPPORT APPARATUS WITH A SUPPORT PLATE AND AN OVERLAY FOR THE SUPPORT PLATE

(71) Applicant: Siemens Healthcare GmbH, Erlangen (DE)

(72) Inventors: Ulrich Batzer, Buckenhof (DE); Minh-Duc Doan, Erlangen (DE)

(73) Assignee: SIEMENS HEALTHCARE GMBH, Erlangen ( * ) Notice: Subject to any disclaimer, the term of this patent is extended or adjusted under 35 U.S.C. 154(b) by 31 days.

(21) Appl. No.: 15/256,812

(22) Filed: Sep. 6, 2016

(65) Prior Publication Data
US 2017/0079590 A1   Mar. 23, 2017

(30) Foreign Application Priority Data
Sep. 23, 2015 (DE) .................. 10 2015 218 298

(51) Int. Cl.
A61B 5/00 (2006.01)
A61B 5/0408 (2006.01)
A61B 6/04 (2006.01)
A61B 5/0402 (2006.01)
H05F 3/02 (2006.01)
A61N 1/14 (2006.01)

(52) U.S. Cl.
CPC .......... *A61B 5/6892* (2013.01); *A61B 5/0402* (2013.01); *A61B 5/04085* (2013.01); *A61B 6/0407* (2013.01); *A61B 6/0442* (2013.01); *H05F 3/02* (2013.01); *A61B 2560/0468* (2013.01); *A61B 2562/0214* (2013.01); *A61B 2562/182* (2013.01); *A61N 1/14* (2013.01)

(58) Field of Classification Search
None
See application file for complete search history.

(56) References Cited

U.S. PATENT DOCUMENTS

| 3,991,746 A | 11/1976 | Hanna |
| 4,320,766 A | 3/1982 | Alihanka et al. |
| 2003/0136201 A1 | 7/2003 | Hubbard |
| 2009/0289800 A1 | 11/2009 | Hansen |

OTHER PUBLICATIONS

German Decision to Grant and English translation thereof dated Nov. 9, 2016.
Crone, B.: "Common-Mode Rejection: How It Relates to ECG Subsystems and the Techniques Used to Provide Superior Performance", Technical Article, In: http://www.analog.com/static/imported-files/tech_articles/MS-2125.pdf, pp. 1-4; 2011.

*Primary Examiner* — Brian T Gedeon
(74) *Attorney, Agent, or Firm* — Harness, Dickey & Pierce, P.L.C.

(57) ABSTRACT

An arrangement is disclosed including a patient support apparatus with a support plate and an overlay for the support plate. In an embodiment, the support plate or overlay includes an electrically conductive first layer. The first layer is connected and/or connectable to a contact-making apparatus via a first electric transmission path. The contact-making apparatus is connected and/or connectable to a ground or mass via a second electric transmission path. And, in an operating mode of the arrangement in which a patient is supported on the patient support apparatus, the first layer is connected and/or connectable to the patient via a third electric transmission path.

27 Claims, 7 Drawing Sheets

ARRANGEMENT COMPRISING A PATIENT SUPPORT APPARATUS WITH A SUPPORT PLATE AND AN OVERLAY FOR THE SUPPORT PLATE

PRIORITY STATEMENT

The present application hereby claims priority under 35 U.S.C. § 119 to German patent application number DE 102015218298.3 filed Sep. 23, 2015, the entire contents of which are hereby incorporated herein by reference.

FIELD

At least one embodiment of the invention generally relates to an arrangement comprising a patient support apparatus with a support plate and an overlay for the support plate.

BACKGROUND

When measuring a bioelectric signal, for example an electrocardiogram signal (ECG signal), via a differential voltage measuring system, interference can occur due to a common-mode interference signal. Typically, the greater the difference of a first measuring path of the differential voltage measuring system from a second measuring path of the differential voltage measuring system with respect to the impedance, the stronger the common-mode interference signal.

If the first measuring path and the second measuring path are in each case in contact with the patient's skin via electrodes, the difference with respect to the impedance can be particularly high. In many cases, the establishment of the same conditions, in particular the same impedances, at two or more electrode contact points on a patient and their maintenance throughout the duration of a measurement represents a challenge. [BC11] discloses various possibilities for the suppression of a common-mode interference signal.

SUMMARY

At least one embodiment of the invention enables improved suppression of a common-mode interference signal.

At least one embodiment of the invention is directed to an arrangement. The arrangement according to at least one embodiment of the invention comprises a patient support apparatus with a support plate and an overlay for the support plate, wherein the support plate or the overlay comprises an electrically conductive first layer, wherein the first layer is connected and/or is connectable to a contact-making apparatus via a first electric transmission path, wherein the contact-making apparatus is connected and/or is connectable to a ground or mass via a second electric transmission path, and wherein, in an operating mode of the arrangement, in which a patient is supported on the patient support apparatus, the first layer is connected and/or is connectable to the patient via a third electric transmission path.

BRIEF DESCRIPTION OF THE DRAWINGS

The invention is described again in more detail below with reference to the attached figures and with reference to example embodiments. The depiction in the figures is schematic, greatly simplified and not necessarily true to scale.

The figures show.

DETAILED DESCRIPTION OF THE EXAMPLE EMBODIMENTS

Figure 1:
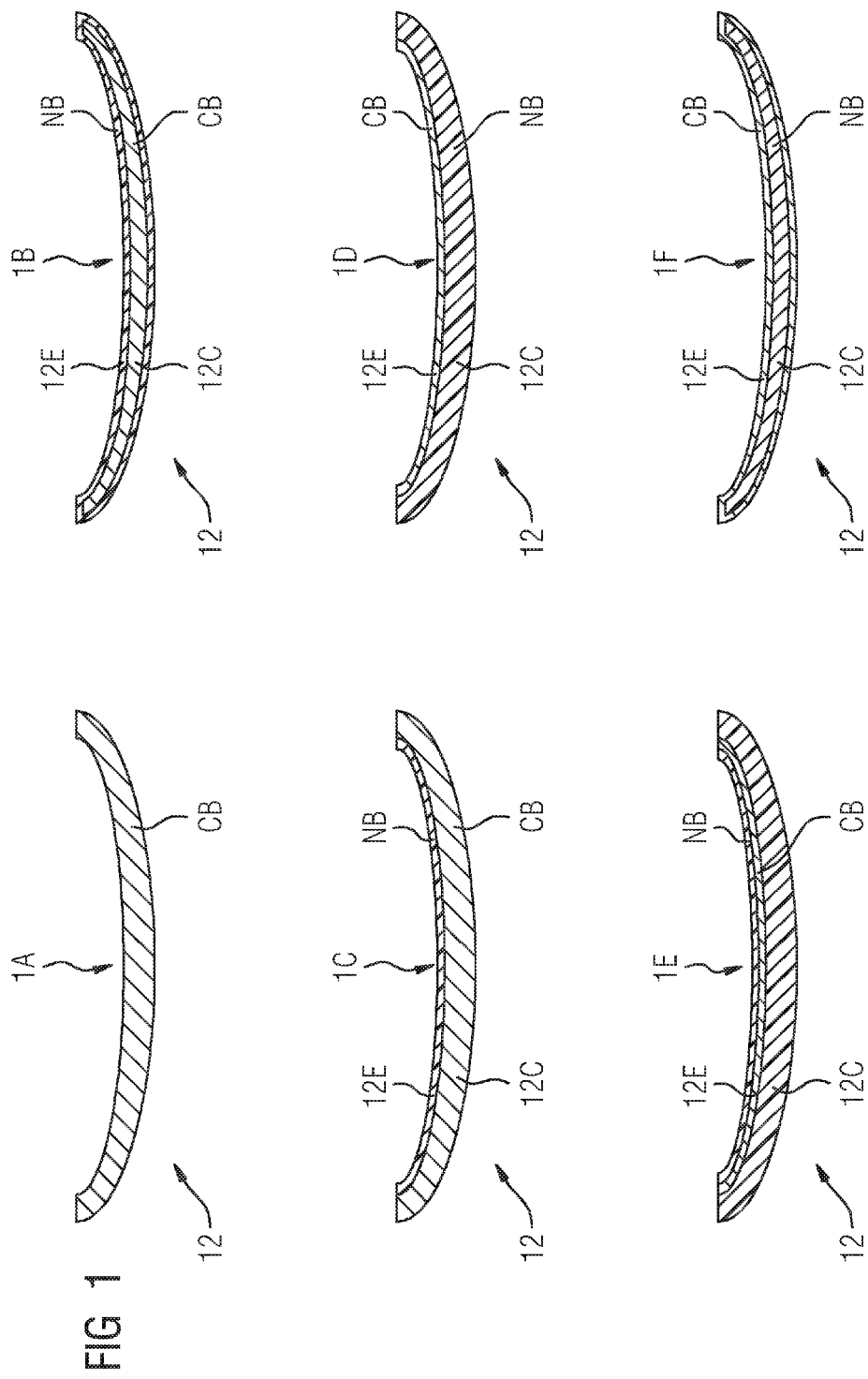
FIG. 1 several examples of a support plate with an electrically conductive layer, FIG. 2 several examples of an overlay with an electrically conductive layer, FIG. 3 an arrangement according to a first embodiment of the invention, FIG. 4 an arrangement according to a second embodiment of the invention, FIG. 5 an arrangement according to a third embodiment of the invention, FIG. 6 an arrangement according to a fourth embodiment of the invention, FIG. 7 an arrangement according to a fifth embodiment of the invention, FIG. 8 a schematic depiction of an arrangement according to a sixth embodiment of the invention, FIG. 9 an arrangement according to a seventh embodiment of the invention.

In the following, embodiments of the invention are described in detail with reference to the accompanying drawings. It is to be understood that the following description of the embodiments is given only for the purpose of illustration and is not to be taken in a limiting sense. It should be noted that the drawings are to be regarded as being schematic representations only, and elements in the drawings are not necessarily to scale with each other. Rather, the representation of the various elements is chosen such that their function and general purpose become apparent to a person skilled in the art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to an arrangement. The arrangement according to at least one embodiment of the invention comprises a patient support apparatus with a support plate and an overlay for the support plate, wherein the support plate or the overlay comprises an electrically conductive first layer, wherein the first layer is connected and/or is connectable to a contact-making apparatus via a first electric transmission path, wherein the contact-making apparatus is connected and/or is connectable to a ground or mass via a second electric transmission path, and wherein, in an operating mode of the arrangement, in which a patient is supported on the patient support apparatus, the first layer is connected and/or is connectable to the patient via a third electric transmission path.

The support plate can, for example, have a planar component and/or be curved. The overlay can, for example, have a planar structure and/or be flexible. In the operating mode of the arrangement in which the patient is supported on the patient support apparatus, the overlay is arranged between the support plate and the patient such that the overlay lies on the support plate and the patient lies on the overlay.

The support plate in particular comprises a given layer when an area defined by the given layer and an area defined by the support plate are arranged in parallel or substantially in parallel. The overlay in particular comprises a given layer when an area defined by the given layer and an area defined by the overlay are arranged in parallel or substantially in parallel. One embodiment of the invention provides that the patient support apparatus comprises the overlay.

One embodiment of the invention provides that an electrically conductive layer can in particular be conducting. An electric transmission path can in particular be understood to be a path in which an electric current, in particular an electric alternating current, can flow and/or an electric power can be transmitted. An electric transmission path typically comprises one or more sections. For purposes of simplicity, each of these sections can in each case be treated or described as an electronic component, wherein the electronic component has a complex impedance with a real, resistive component and/or with an imaginary, capacitive or inductive component.

The inventors have recognized that, with the aid of a support plate of a patient support apparatus and/or an overlay for the support plate, an electric transmission path connecting the patient to a ground or mass can be implemented with lower impedance. The inventors suggest the implementation of a capacitively coupling and/or electrically conducting section of the transmission path with the aid of an electrically conductive layer. This enables a level of an interference signal in the patient and/or a current that gives rise to a common mode interference signal in the differential voltage measuring system to be reduced.

According to one embodiment of the invention, the support plate or the overlay comprises an electrically non-conductive second layer, wherein the second layer forms a capacitively coupling section of the third transmission path. This enables a high current flow, for example in the case of electrostatic charging or contact with an external voltage source, from the patient to the overlay to be avoided.

One embodiment of the invention provides that an electrically non-conductive layer can in particular be insulating and/or static dissipative and/or antistatic conductive. One embodiment of the invention provides that the support plate comprises the first layer and/or that the overlay comprises the second layer. In this context the overlay preferably has the highest possible relative permittivity. This enables the greatest possible capacitance of the capacitively coupling section of the third transmission path to be achieved.

According to one embodiment of the invention the overlay comprises an overlay core region and/or an overlay edge region, wherein the overlay core region comprises the first layer and/or the overlay edge region comprises the second layer. One embodiment of the invention provides that the overlay core region comprises the second layer and/or that the overlay edge region comprises the first layer. One embodiment of the invention provides that, in the operating mode of the arrangement in which the patient is supported on the patient support apparatus, the overlay edge region is arranged between the patient and the overlay core region or between the overlay core region and the support plate.

The overlay core region can in particular be an inner material of the overlay. The overlay core region can, for example, be a mat. The overlay core region can in particular comprise a pad and/or be padded and/or embodied for the padded support of the patient. The overlay core region can, for example, be made of plastic foam. The plastic foam can in particular be electrically conductive or electrically non-conductive.

The overlay edge region can in particular be an outer material of the overlay. The overlay edge region can, for example, be an overlay sleeve and/or an overlay cover layer. The overlay edge region can in particular be designed to improve the durability and/or to improve the biocompatibility of the overlay. The overlay edge region can in particular be a plastic film. The plastic film can in particular be electrically conductive or electrically non-conductive. In particular when the overlay edge region is non-conductive, the color of the overlay edge regions can be selected from a particularly wide range of colors.

The overlay edge region can, for example, be connected detachably or non-detachably to the overlay core region. The overlay edge region, for example the plastic film, can in particular lie on the overlay core region and/or enclose the overlay core region. One embodiment of the invention provides that the overlay core region is a mat made of conductive foam and/or that an electrically non-conductive overlay edge region can optionally be arranged on the overlay core region.

In particular, the overlay can be a multipart structure with one or more overlay inner layers and one or more overlay outer layers. The overlay inner layers and the overlay outer layers can for example be combined flexibly. The first layer can, for example, be a first overlay inner layer or a first overlay outer layer. The second layer can, for example, be a second overlay inner layer or a second overlay outer layer. The one or more overlay inner layers can form the overlay core region. The one or more overlay outer layers can form the overlay edge region. It would also be conceivable to form the first layer by way of doping and/or the introduction of conductive particles and/or fibers into the overlay.

According to one embodiment of the invention, the first layer forms a non-conductive recess, wherein one or more electric lines are arranged or can be arranged on the overlay in a region defined by the recess. Alternatively or additionally, an electric component, for example of a differential voltage measuring system and/or an ECG system, can be arranged or arrangeable on the overlay in the region defined by the recess region. The electric component can in particular be connected to the one or more electric lines. This in particular enables parasitic capacitances between the first layer on the one hand and the one or more electric lines and/or the electric component on the other to be reduced. The region defined by the recess can, for example, be marked by a color and/or with the aid of a mold and/or a pattern.

According to one embodiment of the invention, the recess extends in a longitudinal direction of the overlay. One embodiment of the invention provides that, in the operating mode of the arrangement in which the patient is supported on the patient support apparatus, the longitudinal direction of the patient, the longitudinal direction of the overlay and the longitudinal direction of the support plate coincide.

According to one embodiment of the invention, the contact-making apparatus comprises a first connection partner of a detachable electric connection, wherein the second transmission path comprises a second connection partner of the detachable electric connection corresponding to the first connection partner. In particular, the contact-making apparatus can be conductive and/or conducting. In particular when the support plate does not have an electrically conductive layer, this enables the first layer to be connected to a ground or mass via the detachable electric connection. The detachable electric connection can, for example, be a ground connection with a socket and plug.

According to one embodiment of the invention, the support plate comprises an electrically conductive third layer, wherein the contact-making apparatus comprises the third layer. According to one embodiment of the invention, the support plate comprises an electrically non-conductive fourth layer, wherein the fourth layer forms a capacitively coupling section of the first transmission path.

According to one embodiment of the invention the support plate comprises a support plate core region and/or a support plate edge region, wherein the support plate core region comprises the first layer and/or the third layer and/or the support plate edge region comprises the second layer and/or the fourth layer. One embodiment of the invention provides that the support plate core region comprises the fourth layer and/or that the support plate edge region comprises the third layer. One embodiment of the invention provides that, in the operating mode of the arrangement in which the patient is supported on the patient support apparatus, the support plate edge region is arranged between the overlay and the support plate core region.

The support plate core region can in particular be an inner material of the support plate. The support plate core region can in particular endow the support plate with high strength and/or a high degree of rigidity. The support plate core region can, for example, be a planar component, for example made of plastic. The plastic can in particular be electrically conductive or electrically non-conductive.

The support plate edge region can in particular be an outer material of the support plate. The support plate edge region can, for example, be a support plate sleeve and/or a support plate cover layer. The support plate edge region can in particular be designed to improve the durability and/or to improve the biocompatibility of the support plate. In particular, the support plate edge region can be a plastic film. The plastic film can in particular be electrically conductive or electrically non-conductive.

The support plate edge region can, for example, be connected detachably or non-detachably to the support plate core region. The support plate edge region, for example the plastic film, can in particular lie on the support plate core region and/or enclose the support plate core region. One embodiment of the invention provides that the support plate core region is a planar component made of conductive plastic and/or that an electrically non-conductive support plate edge region can optionally be arranged on the support plate core region.

In particular, the support plate can be a multi-part structure with one or more support plate inner layers and one or more support plate outer layers. The support plate inner layers and the support plate outer layers can, for example, be combined flexibly. The first layer can, for example, be a first support plate inner layer or a second support plate outer layer. The second layer can, for example, be a second support plate inner layer or a second support plate outer layer. The one or more support plate inner layers can form the support plate core region. The one or more support plate outer layers can form the support plate edge region. It would also be conceivable to form the first layer and/or the third layer by way of doping and/or the introduction of conductive particles and/or fibers into the overlay.

According to one embodiment of the invention, the specific surface resistivity of the first layer is greater than 100 Ohm and/or lower than 1 mega-ohm and/or the surface resistivity of the third layer is greater than 100 Ohm and/or lower than 1 mega-ohm. According to one embodiment of the invention, the surface resistivity of the second layer is greater than 1 mega-ohm and/or lower than 1 giga-ohm and/or the surface resistivity of the fourth layer is greater than 1 mega-ohm and/or lower than 1 giga-ohm.

One embodiment of the invention provides that the surface resistivity of the first layer is greater than 1 kilo-ohm and/or lower than 100 kilo-ohm, preferably lower than 10 kilo-ohm and/or that the surface resistivity of the third layer is greater than 1 kilo-ohm and/or lower than 100 kilo-ohm, preferably lower than 10 kilo-ohm. One embodiment of the invention provides that the surface resistivity of the second layer is greater than 1 giga-ohm and/or lower than 1 tera-ohm and/or the surface resistivity of the fourth layer is greater than 1 giga-ohm and/or lower than 1 tera-ohm. A surface resistivity greater than 100 Ohm, preferably greater than 1 kilo-ohm, can be advantageous with respect to electrostatic discharge.

According to one embodiment of the invention, the relative permittivity of the second layer is greater than 5, in particular greater than 10, preferably greater than 20. According to one embodiment of the invention, the relative permittivity of the fourth layer is greater than 5, in particular greater than 10, preferably greater than 20. One embodiment of the invention provides that the relative permittivity relates to a frequency of 50 hertz. If the second layer and/or the fourth layer in each case are made of different materials, relative permittivity should be understood to mean the resultant relative permittivity.

According to one embodiment of the invention, the second layer and/or the fourth layer are made of latex and/or made of plastic. Latex can have a very high relative permittivity.

According to one embodiment of the invention, the capacitive component of the impedance of a transmission path is selected from the group consisting of the first transmission path, the second transmission path, the third transmission path and combinations thereof is greater than 100 pico-farad and/or lower than 100 nano-farad. One embodiment of the invention provides that the capacitive component of the impedance of a transmission path is selected from the group consisting of the first transmission path, the second transmission path, the third transmission path and combinations thereof is greater than 1 nano-farad and/or lower than 10 nano-farad, preferably lower than 5 nano-farad. One embodiment of the invention provides that the capacitive component of the impedance of the electric transmission path formed from the first transmission path, the second transmission path, the third transmission path, the first layer and the contact-making apparatus is greater than 100 pico-farad, preferably greater than 1 nano-farad and/or lower than 100 nano-farad, preferably lower than 10 nano-farad.

According to one embodiment of the invention, the resistive component of the impedance of a transmission path is selected from the group consisting of the first transmission path, the second transmission path, the third transmission path and combinations thereof is greater than 100 Ohm and/or lower than 1 mega-ohm. One embodiment of the invention provides that the resistive component of the impedance of a transmission path is selected from the group consisting of the first transmission path, the second transmission path, the third transmission path and combinations thereof is greater than 1 kilo-ohm and/or lower than 100 kilo-ohm, preferably lower than 10 kilo-ohm. One embodiment of the invention provides that the resistive component of the impedance of the electric transmission path formed from the first transmission path, the second transmission path, the third transmission path, the first layer and the contact-making apparatus is greater than 100 Ohm, preferably greater than 1 kilo-ohm, and/or lower than 1 mega-ohm, preferably lower than 100 kilo-ohm.

One embodiment of the invention provides that the second transmission path comprises an electric line embodied for connection to the ground and/or mass. A resistive component of the impedance of a transmission path that is greater than 100 Ohm, preferably greater than 1 kilo-ohm, can be advantageous with respect to electrostatic discharge. The ground can, for example, be provided by a grounded support table of the patient support apparatus. One embodiment of the invention provides that the impedance in each case relates to a frequency of 50 hertz.

According to one embodiment of the invention, the support plate and/or the overlay is transparent to X-rays from an X-ray source in a medical imaging apparatus. The support plate can be made of one or more X-ray transparent materials. The overlay can be made of one or more X-ray transparent materials. An X-ray transparent material can, for example, be carbon, a plastic or a non-metallic material.

According to one embodiment of the invention, the support plate and/or the overlay comprises a region made from one or more plastics and/or one or more carbon-containing and/or carbon-fiber reinforced materials, wherein the region comprises a layer selected from the group consisting of the first layer the second layer, the third layer and the fourth layer. One embodiment of the invention provides that the region is selected from the group consisting of the overlay core region, the overlay edge region, the support plate core region and the support plate edge region. The region can in particular comprise one or more conductive additives forming the first layer and/or the third layer. The plastic or plurality of plastics can in particular be X-ray transparent and/or carbon-containing and/or carbon-fiber-reinforced. The one or the plurality of carbon-containing and/or carbon-fiber reinforced materials can in particular be X-ray transparent.

According to one embodiment of the invention, the first layer and/or the third layer is selected from the group consisting of a conductive plastic layer, a conductive plastic foam layer, a conductive plastic film, a conductive textile layer, a conductive fabric layer and combinations thereof. In particular, conductive fibers embedded or woven into in a textile and/or a fabric can form a first layer and/or a third layer. The plastic used can in particular be polyurethane and/or polyethylene. The plastic can in particular comprise one or more conductive additives.

According to one embodiment of the invention, the arrangement according to the invention comprises a differential voltage measuring system for measuring a bioelectric signal, wherein, in the operating mode of the arrangement in which the patient is supported on the patient support apparatus, a first electric measuring path of the differential voltage measuring system and a second electric measuring path of the differential voltage measuring system, are connected or can be connected to the patient. One embodiment of the invention provides that the bioelectric signal is a bioelectric signal from the patient. One embodiment of the invention provides that the differential voltage measuring system is an electrocardiogram system (ECG system) and/or that the bioelectric signal is an electrocardiogram signal (ECG signal).

One embodiment of the invention provides that the differential voltage measuring system comprises a first input and a second input, wherein the first input and the second input form a differential input stage of the voltage measuring system, that the first measuring path is connected to the first input and that the second measuring path is connected to the second input.

According to one embodiment of the invention, the first measuring path comprises a first electric line and the second measuring path a second electric line, wherein the first line and/or the second line are arranged or can be arranged on the overlay in the region defined by the recess.

According to one embodiment of the invention, the arrangement according to the invention comprises an imaging apparatus with an acquisition region formed by a tunnel-shaped opening, wherein the patient support apparatus comprises a support table, wherein the support plate is arranged movably relative to the support table on the support table such that the support plate can be introduced into the acquisition region in a longitudinal direction of the support plate.

According to one embodiment of the invention, the imaging apparatus is selected from the imaging modality group consisting of an X-ray device, a computed tomography device, a C-arm X-ray device, a single photon emission computed tomography device (SPECT device), a positron emission tomography device (PET device), a magnetic resonance tomography device, an ultrasound device and combinations thereof. The imaging apparatus can in particular be a combination of one or more imaging modalities, which are in each case selected from the imaging modality group and/or one or more irradiation modalities, for example a PET-CT device or a SPECT-CT device. In this context, an irradiation modality can, for example, comprise an irradiation apparatus for therapeutic irradiation.

One embodiment of the invention provides that the support plate and/or the overlay is transparent to radiation from a radiation source in the imaging apparatus. One embodiment of the invention provides that the imaging apparatus comprises the patient support apparatus and/or that the patient support apparatus is a patient support apparatus of the imaging apparatus. One embodiment of the invention provides that the mass is a mass of the differential voltage measuring system and/or a mass of the imaging apparatus. The mass can in particular be an electrical conductor.

According to one embodiment of the invention, on a contact surface selected from the contact surface group consisting of a common contact surface of the support plate and the overlay, a common contact surface of the support plate and the support table and a common contact surface of the overlay and the support table, the contact partners of the contact surface are similar or the same with respect to a property, wherein the property is selected from the property group, consisting of material, electron affinity, electron work function, triboelectric charging behavior, a position in the triboelectric series, surface resistance and combinations thereof. This enables the triboelectric effect, in particular electrostatic charging resulting from contact and/or friction of the contact partners, to be reduced and/or avoided.

The invention in particular enables the patient to be connected to the ground or mass via a transmission path with reduced effort. The transmission path is formed, in that the patient is supported on the patient support apparatus. The formation of the transmission path does not require any electrical connections to be applied to and/or fixed on the patient individually. This moreover enables the number of electric lines in the immediate environment of the patient to be reduced. Hence, it is in particular possible to reduce the susceptibility to error of the measurement of the bioelectric signal and/or to increase the freedom of movement or comfort of the patient.

Within the context of the invention, features described with reference to different embodiments and/or different claim categories can be combined to form further embodiments. In other words, the substantive claims can also be developed in conjunction with the features described or claimed in connection with a method. In this context, functional features of the method can be carried out by correspondingly embodied modules.

The use of the indefinite article "a" or "an" does not preclude the possibility of the elements in question also being present on a multiple basis. The use of a given ordinal number in connection with a given element serves to provide better differentiation of the given element from other elements and does not mean that in each case an element has to be present for all the ordinal numbers preceding the given ordinal number. For example, the arrangement according to the invention can comprise a third element, for example the third layer, without a second element, for example the second layer, being present.

The invention is not restricted by the disclosed embodiments and examples. Further variations can be derived by the person skilled in the art without departing from the scope of the invention as defined by the claims.

FIG. 1 shows several examples of a support plate 12 with an electrically conductive layer CB. Each case is a schematic depiction of a cross section perpendicular to a longitudinal direction of the support plate 12.

The support plate 12 according to Example 1A comprises an electrically conductive layer CB. The example 1A provides that the support plate 12 is made of a conductive material, which in particular forms the layer CB.

The support plate 12 according to Example 1B comprises a support plate core region 12C with an electrically conductive layer CB and a support plate edge region 12E with an electrically non-conductive layer NB. Example 1B provides that the support plate core region 12C is made of a conductive material, which in particular forms the layer CB, and that the support plate core region 12C is enclosed by a non-conductive support plate sleeve forming the support plate edge region 12E, in particular the layer NB.

The support plate 12 according to Example 1C comprises a support plate core region 12C with an electrically conductive layer CB and a support plate edge region 12E with an electrically non-conductive layer NB. Example 1C provides that the support plate core region 12C is made of a conductive material which in particular forms the layer CB and that, on a side provided to accommodate an overlay 15, the support plate core region 12C is covered by a support plate cover layer that forms the support plate edge region 12E, in particular the layer NB.

The support plate 12 according to Example 1D comprises a support plate edge region 12E with an electrically conductive layer CB. Example 1D provides that, on a side provided to accommodate an overlay 15, the support plate core region 12C is covered by a support plate cover layer that forms the support plate edge region 12E, in particular the layer CB.

The support plate 12 according to Example 1E comprises a support plate edge region 12E with an electrically conductive layer CB and an electrically non-conductive layer NB. Example 1E provides that, on a side which is provided to accommodate an overlay 15, the support plate core region 12C is covered by a multilayer support plate cover layer that forms the support plate edge region 12E, in particular the layer CB and the layer NB.

The support plate 12 according to Example 1F comprises a support plate edge region 12E with an electrically conductive layer CB. Example 1F provides that the support plate core region 12C is enclosed by a conductive support plate sleeve that forms the support plate edge region 12E, in particular the layer CB.

Figure 2:
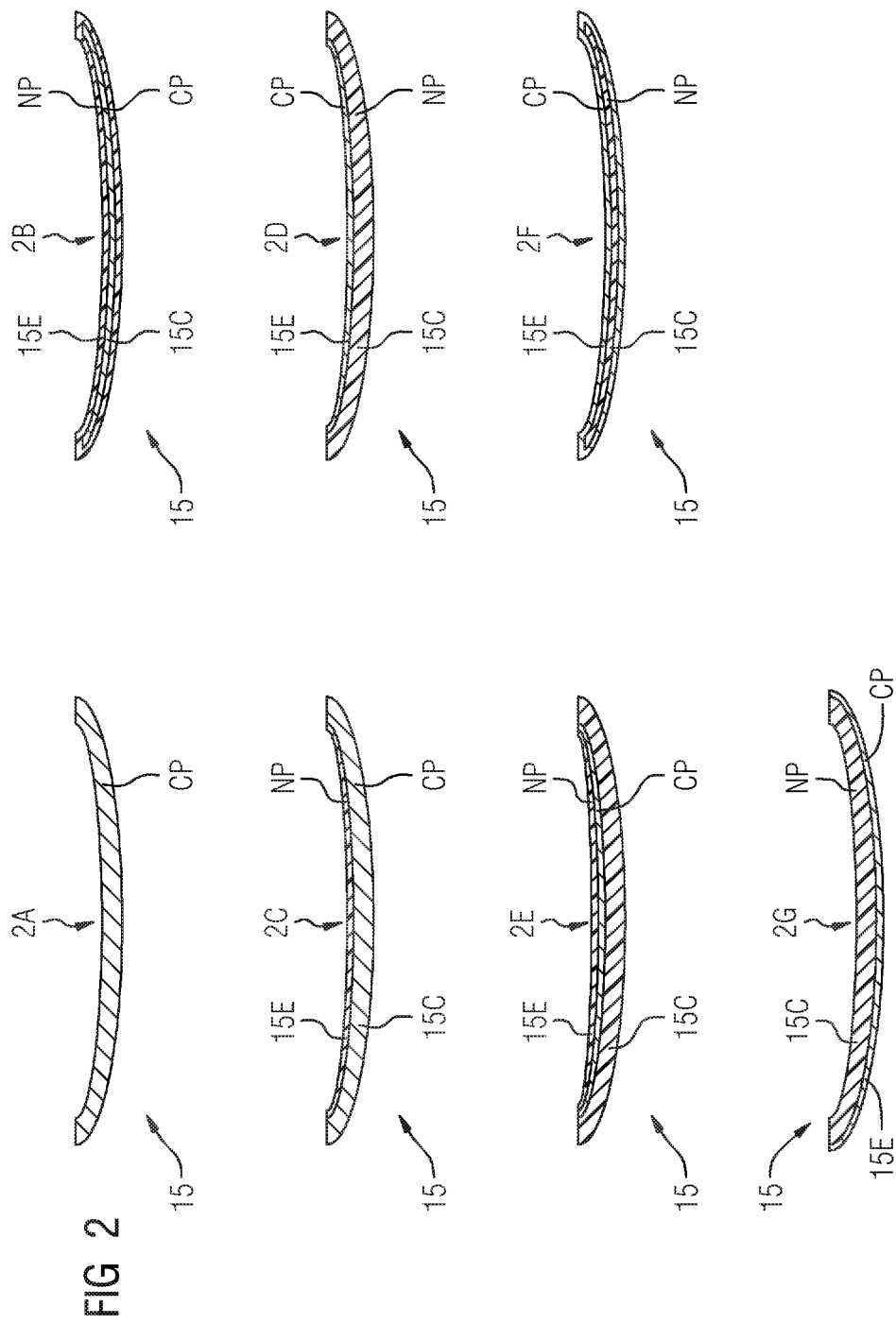

FIG. 2 shows several examples of an overlay 15 with an electrically conductive layer CP. Each case is a schematic depiction of a cross section perpendicular to a longitudinal direction of the overlay 15.

The overlay 15 according to Example 2A comprises an electrically conductive layer CP. Example 2A provides that the overlay 15 is made of a conductive material that in particular forms the layer CP.

The overlay 15 according to Example 2B comprises an overlay core region 15C with an electrically conductive layer CP and an overlay edge region 15E with an electrically non-conductive layer NP. Example 2B provides that the overlay core region 15C is made of a conductive material that in particular forms the layer CP and that the overlay core region 15C is enclosed by a non-conductive overlay sleeve that forms the overlay edge region 15E, in particular the layer NP.

The overlay 15 according to Example 2C comprises an overlay core region 15C with an electrically conductive layer CP and an overlay edge region 15E with an electrically non-conductive layer NP. Example 2C provides that the overlay core region 15C is made of a conductive material that in particular forms the layer CP and that, on a side provided to accommodate a patient 13, the overlay core region 15C is covered by an overlay cover layer that forms the overlay edge region 15E, in particular the layer NP.

The overlay 15 according to Example 2D comprises an overlay edge region 15E with an electrically conductive layer CP. Example 2D provides that, on a side provided to accommodate a patient 13, the overlay core region 15C is covered by an overlay cover that forms the overlay edge region 15E, in particular the layer CP.

The overlay 15 according to Example 2E comprises an overlay edge region 15E with an electrically conductive layer CP and an electrically non-conductive layer NP. Example 2E provides that, on a side provided to accommodate a patient 13, the overlay core region 15C is covered by a multilayer overlay cover layer that forms the overlay edge region 15E, in particular the layer CP and the layer NP.

The overlay 15 according to Example 2F comprises an overlay edge region 15E with an electrically conductive layer CP. Example 2F provides that the overlay core region 15C is surrounded by a conductive sleeve that forms the overlay edge region 15E, in particular the layer CP.

The overlay 15 according to Example 2G comprises an overlay edge region 15E with an electrically conductive layer CP. Example 2G provides that, on a side provided for placing on the support plate 12, the overlay core region 15C is covered by an overlay cover layer forming the overlay edge region 15E, in particular the layer CP.

In FIGS. 3 to 9, the arrangement 1 is in each case shown in the operating mode in which the patient 13 is supported on the patient support apparatus 10.

Figure 3:
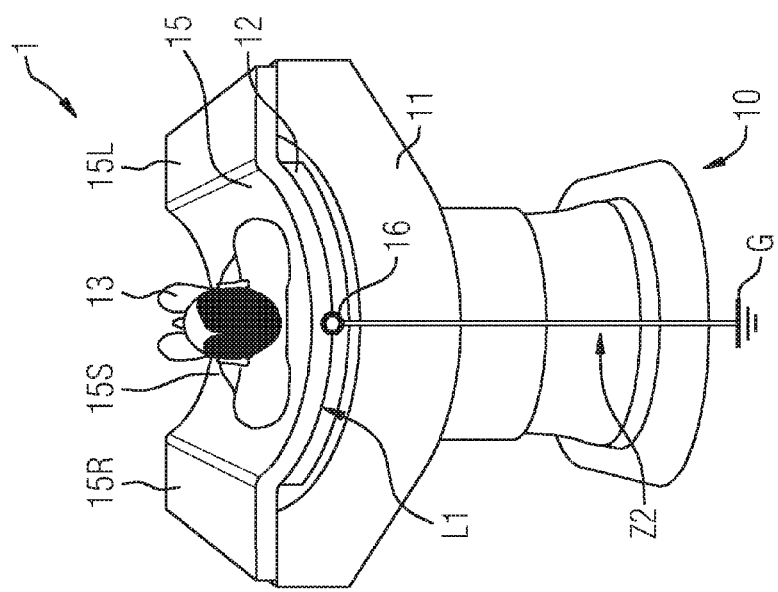

FIG. 3 shows an arrangement 1 according to a first embodiment of the invention. The arrangement 1 comprises a patient support apparatus 10 with a support plate 12 and an overlay 15 for the support plate 12. The patient support apparatus 10 is embodied to support the patient 13. The support plate 12 arranged is on a support table 11.

The support plate 12 is selected from the support plate group consisting of the support plate 12 according to Example 2A, the support plate 12 according to Example 2B, the support plate 12 according to Example 2C, the support plate 12 according to Example 2D the support plate 12 according to Example 2E and the support plate 12 according to Example 2F and/or the overlay 15 is selected from the overlay group consisting of the overlay 15 according to Example 2A, the overlay 15, according to Example 2B, the overlay 15 according to Example 2C, the overlay 15 according to Example 2D, the overlay 15 according to Example 2E, the overlay 15 according to Example 2F and the overlay 15 according to Example 2G.

The layer CB can be the electrically conductive first layer L1 or the electrically conductive third layer L3. The layer CP can be the first layer L1 or the third L3 layer. The layer NB can be the electrically non-conductive second layer L2 or the electrically non-conductive fourth layer L4. The layer NP can be the second layer L2 or the fourth layer L4.

If the overlay 15 comprises the first layer L1, it is not necessary for the support plate 12 to comprise an electrically conductive layer. If the support plate 12 comprises the first layer L1, it is not necessary for the overlay 15 to comprise an electrically conductive layer. In particular if the support plate 12 the first layer L1, the overlay 15 can optionally be made of a non-conductive material with a high relative permittivity and/or comprise the second layer L2.

The first layer L1 is connected and/or can be connected via a first electric transmission path Z1 to a contact-making apparatus 16. The contact-making apparatus 16 is connected and/or can be connected via a second electric transmission path Z2 to a ground G and/or a mass. In the operating mode of the arrangement 1 in which the patient 13 is supported on the patient support apparatus 10, the first layer L1 is connected and/or can be connected via a third electric transmission path Z3 to the patient 13.

Figure 4:
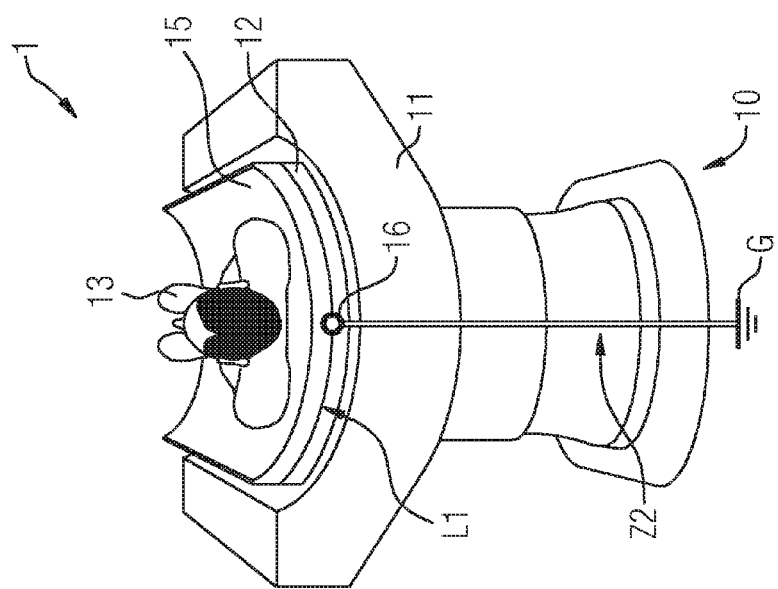

FIG. 4 shows an arrangement 1 according to a second embodiment of the invention.

The second embodiment of the invention provides that, in a transverse direction of the overlay 15, the extension of the overlay 15 overshoots the extension the support plate 12 in a transverse direction of the support plate 12 such that, in an operating mode of the arrangement 1 in which the overlay 15 is arranged on the support plate 12, a gap located with respect to the transverse direction of the support plate 12 between the support plate 12 and the support table 11 and which extends in a longitudinal direction of the support plate 12 can be bridged by way of the overlay 15.

The second embodiment of the invention provides that, in addition to a patient support region 15S S which is provided to accommodate the patient 13, the overlay 15 comprises a first wing region 15R and a second wing region 15L, wherein the patient support region 15S is located with respect to the transverse direction between the first wing region 15R and the second wing region 15L. In the transverse direction of the overlay 15, the first wing region 15R adjoins the support region 15S an. On a side lying opposite to the first wing region 15R, the second wing region 15L adjoins the patient support region 15S in the transverse direction of the overlay 15. A transverse direction of the support plate 12 can in particular be a direction perpendicular to the longitudinal direction of the support plate 12. A transverse direction of the overlay 15 can in particular be a direction perpendicular to the longitudinal direction of the overlay 15. In the operating mode of the arrangement 1 in which the patient 13 is supported on the patient support apparatus 10, the transverse direction the support plate 12 and the transverse direction of the overlay 15 are horizontal.

The arrangement 1 according to the second embodiment of the invention is in particular advantageous when the support plate 12 is mounted movably relative to the support table 11, since the bridging of the gaps by way of the overlay 15 enables a reduction of the influences and dangers of a movement of the patient 13 and/or a device connected to the patient 13, for example an electric line W1, W2, relative to the support table 11.

Figure 5:
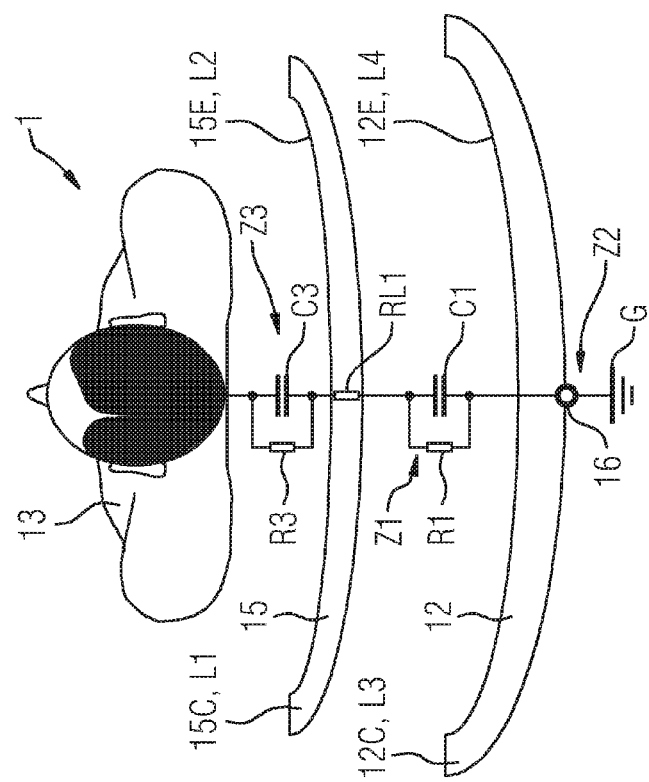

FIG. 5 shows an arrangement 1 according to a third embodiment of the invention. The third embodiment of the invention provides that the overlay 15 comprises the layer L1 and is connected to the contact-making apparatus 16 via an electric connection that forms the first transmission path Z1. The arrangement 1 comprises the contact-making apparatus 16, which is connected and/or can be connected via the second transmission path Z2, for example in the form of an electric line, to a ground G and/or a mass. The contact-making apparatus 16 comprises a first connection partner, for example in the form of a socket, of a detachable electric connection. The second transmission path Z2 comprises a second connection partner corresponding to the first connection partner, for example in the form of a plug.

The first layer L1 forms a resistance RL1 arranged between the third transmission path Z3 and the first transmission path Z1. The value of the resistance RL1 can in particular be dependent on the surface resistivity and/or the material resistance of the first layer L1. According to the third embodiment of the invention, the value of the resistance RL1 is greater than 100 Ohm, preferably greater than 1 kilo-ohm, and lower than 1 mega-ohm, preferably lower than 100 kilo-ohm.

The patient 13 and the first layer L1 form a capacitance C3 and resistance R3 arranged in parallel to the capacitance C3. The capacitance C3 and the resistance R3 form a section of the third transmission path Z3. The value of the capacitance C3 can in particular be dependent on the dimensions of the patient 13, the dimensions of the first layer L1 and a material composition arranged between the patient 13 and the first layer L1, for example clothing and/or sanitary material, and the dimensions thereof. The value of the capacitance C3 is between 100 pico-farad and 100 nano-farad. In particular when the patient 13 is in direct contact with the first layer L1, the value of the resistance R3 can be lower than 1 giga-ohm, in particular lower than 10 mega-ohm, preferably lower than 1 mega-ohm.

Figure 6:
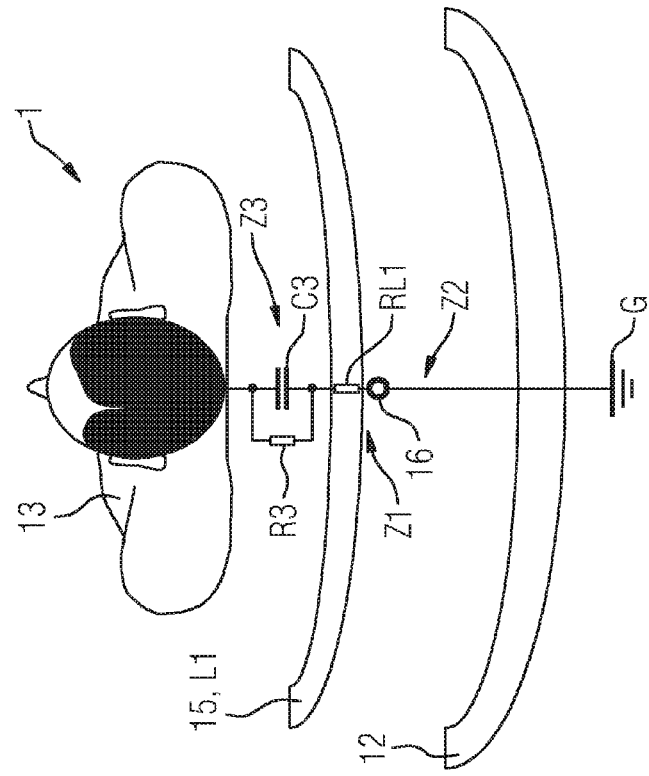

FIG. 6 shows an arrangement 1 according to a fourth embodiment of the invention. The fourth embodiment of the invention provides that the overlay 15 comprises an overlay core region 15C with the first layer L1 and an overlay edge region 15E with the second layer L2 and that the support plate 12 comprises a support plate core region 12C with the third layer L3 and a support plate edge region 12E with the fourth layer L4. The second layer L2 forms a capacitively coupling section of the third transmission path Z3. The fourth layer L4 forms a capacitively coupling section of the first transmission path Z1. According to the fourth embodiment of the invention, the contact-making apparatus 16 comprises the third layer L3.

The first layer L1 and the third layer L3 form a capacitance C1 and a resistance R1 arranged in parallel to the capacitance C1. The capacitance C1 and the resistance R1 form a section of the first transmission path Z1. The value of the capacitance C1 can in particular depend on the dimensions of the first layer L1, the dimensions of the third layer L3 and a material composition arranged between the first layer L1 and the third layer L3 and the dimensions thereof. The value of the capacitance C1 is between 100 pico-farad and 100 nano-farad. In particular when the first layer L1 is in direct contact with the third layer L3, the value of the resistance R1 can in particular be lower than 1 mega-ohm, in particular lower than 100 kilo-ohm, preferably lower than 10 kilo-ohm.

The value of the capacitance C1 and the value of the capacitance C3 can be estimated in each case with the aid of the formula Q1

$$C = \varepsilon_0 \varepsilon_r \frac{A}{d}. \quad (Q1)$$

C stands for the capacitance, $\varepsilon_0$ stands for the electric field constant. $\varepsilon_r$ stands for the relative permittivity. A stands for a size of the areas, for example a surface of the patient 13 and/or a surface of the support plate 12, which form the capacitance C. d stands for a distance between the areas forming the capacitance C.

Preferably, the materials and dimensions of the arrangement 1 are selected such that the capacitances C1 and C3 are as high as possible. The capacitance C1 and/or C3 can in particular be increased by enlarging the area A. This can, for example, be achieved by the use of an overlay 15 and/or a support plate 12 with a larger supporting surface. The capacitance C1 can in particular be increased by minimizing the distance between the first layer L1 and the third layer L3. This can, for example, be achieved by the use of a thin-walled overlay edge region 15E, in particular a thin-walled overlay sleeve and/or a thin-walled overlay cover layer and/or by the use of a thin-walled support plate edge regions 12E, in particular a thin-walled support plate sleeve and/or a thin-walled support plate cover layer.

The capacitance C3 can in particular be increased by minimizing the distance between the patient 13 and the first layer L1. This can, for example, be achieved by the use of a thin-walled overlay edge regions 15E, in particular a thin-walled overlay sleeve and/or a thin-walled overlay cover layer. In particular, the thickness of a thin-walled overlay edge region 15 can be less than 3 millimeters, preferably less than 1 millimeter.

The capacitance C1 can in particular be increased by increasing the relative permittivity of the material composition arranged between the first layer L1 and the third layer L3. The capacitance C3 can in particular be increased by increasing the relative permittivity of the material composition arranged between the first layer L1 and the patient 13. Materials with a high relative permittivity also enable a high capacitance C3 to be achieved when there is a relatively large distance between the patient 13 and the first layer L1.

Figure 7:
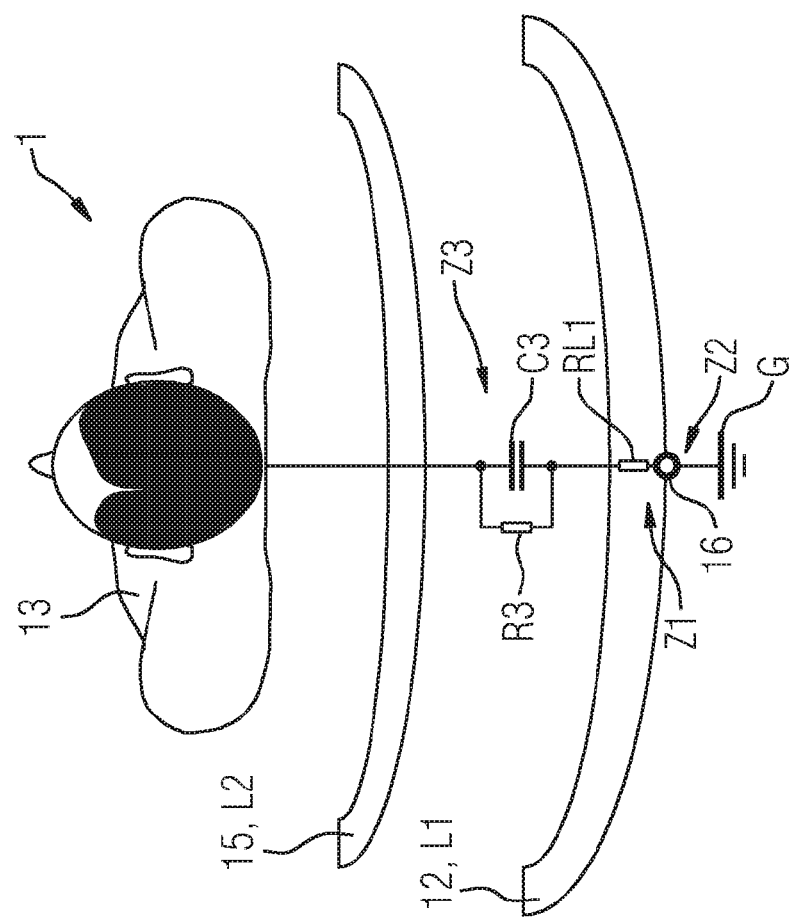

FIG. 7 shows an arrangement according to a fifth embodiment of the invention. The fifth embodiment of the invention provides that the overlay 15 is mainly or completely made of a non-conductive material, for example latex, with a high relative permittivity, that the overlay 15 comprises the second layer L2 and that the support plate 12 comprises the first layer L1. The patient 13 and the first layer L1 form a capacitance C3 and a resistance R3 arranged in parallel to the capacitance C3. The second layer L2 forms a capacitively coupling section of the third transmission path Z3.

The high relative permittivity of the overlay 15 enables a high capacitance C3 to be achieved despite the relatively large distance between the patient 13 and the first layer L1. An overlay 15 which has a thickness of several millimeters or centimeters and is made of non-conductive material with a high relative permittivity enables a higher resistance R3 to be achieved simultaneously with a high capacitance C3. A higher resistance R3 can, for example, be advantageous with respect to a defibrillation application relating to the patient 13 supported on the patient support apparatus 10 and/or with respect to electrostatic discharge and/or with respect to the electric safety, in particular according to the standards relevant for medical technology.

Figure 8:
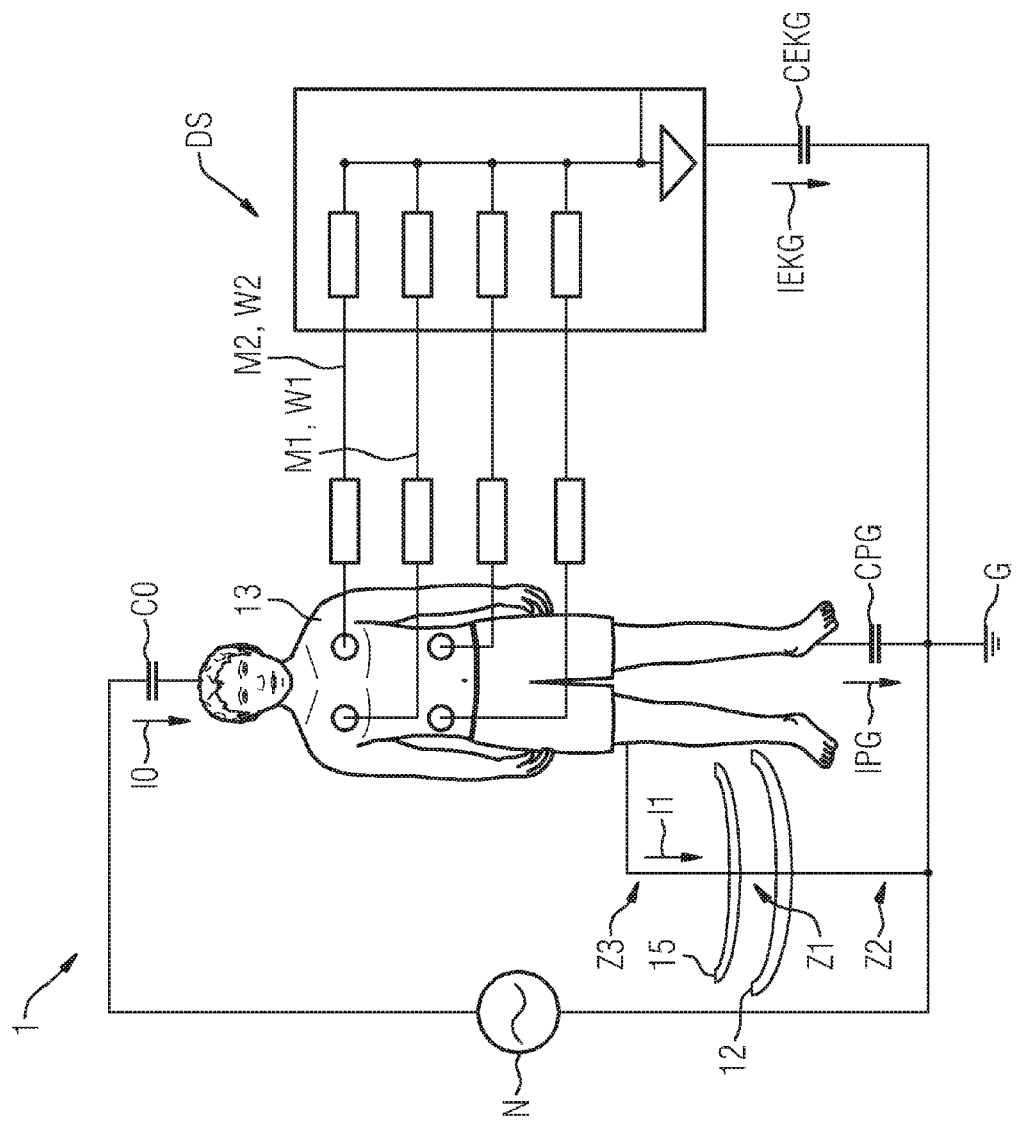

FIG. 8 is a schematic depiction of an arrangement 1 according to a sixth embodiment of the invention. According to the sixth embodiment of the invention, the arrangement 1 comprises a differential voltage measuring system DS, for example an ECG system, for measuring a bioelectric signal, for example an ECG signal, wherein a first electric measuring path M1 of the differential voltage measuring system DS and a second electric measuring path M2 of the differential voltage measuring system DS are connected to the patient 13.

According to an interference model, an interference current I0 from a source of interference N is coupled onto the patient 13 via a first parasitic capacitance C0. The source of interference N relates to a ground G and causes the interference current I0 to flow through the capacitance C0 and the patient 13 to the ground G. The interference current I0 in particular depends upon the first parasitic capacitance C0. The patient 13 is connected to the ground via a plurality of transmission paths. The partial current IEKG of the current I0 flows through the measuring paths M1, M2 of the differential voltage measuring system DS and a second parasitic capacitance CEKG, which is formed by the differential voltage measuring system DS and the ground G, to the ground G. The partial current IEKG gives rise to a common mode interference signal in the differential voltage measuring system DS. The partial current IPG of the current I0 flows through a third parasitic capacitance CPG, which is formed by the patient 13 and the ground G, to the ground G.

The sixth embodiment of the invention provides a further path on which the partial current I1 of the interference current I0 flows through the third transmission path Z3, the first transmission path Z1 and the second transmission path Z2 to the ground G. The interference current I0 is equal to the total of the partial currents I1, IPG and IEKG. The invention in particular enables that I1 to be maximized, for example, by an increase in the capacitance C1 and/or C3 and/or by a reduction of the resistance R1 and/or R3 and/or RL1 so that a large part of the interference current I0 can be discharged in the form of the partial current I1. This enables the partial current IEKG to be reduced and hence the common mode interference signal to be suppressed.

The capacitance CEKG can, for example, be minimized by highly insulating components with low parasitic capacitances and/or a wireless embodiment of the differential voltage measuring system DS and/or a smaller size of components of the differential voltage measuring system DS. This enables the partial current IEKG to be further reduced. Hence, the invention enables improved suppression of a common mode interference signal. First measurements have shown that the arrangement 1 according to the sixth embodiment of the invention enables an additional suppression of a common mode interference signal um 20 dB to 30 dB or better to be achieved.

Figure 9:
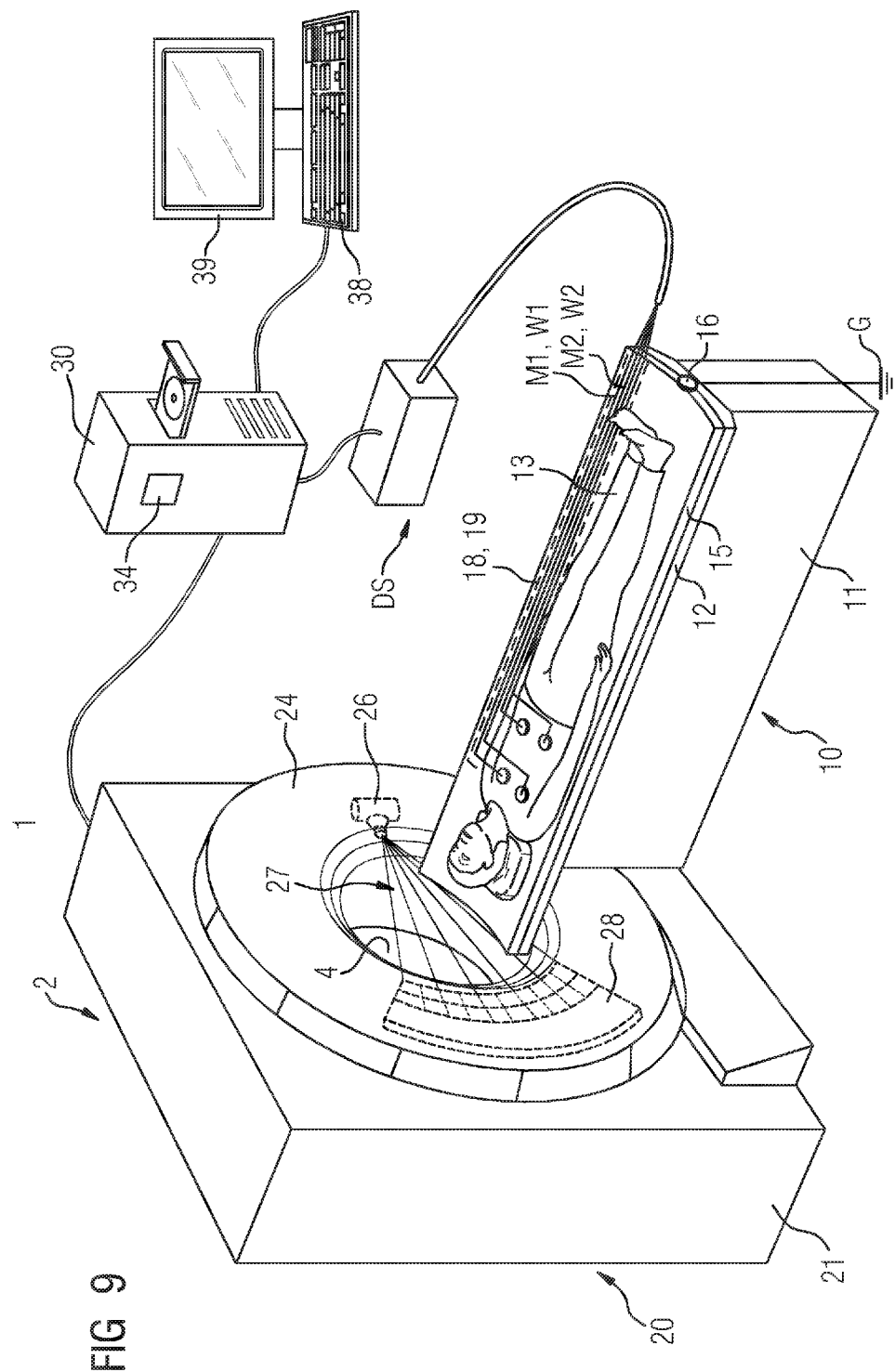

FIG. 9 shows an arrangement 1 according to a seventh embodiment of the invention, wherein the arrangement 1 comprises an imaging apparatus 2 with an acquisition region 4 formed by a tunnel-shaped opening, wherein the patient support apparatus 10 comprises a support table 11, wherein the support plate 12 is arranged relative to the support table 11 movably on the support table such that the support plate 12 can be introduced into the acquisition region 4 in a longitudinal direction of the support plate 12. Without restricting the general concept of the invention, the imaging apparatus 2 shown is by way of example a computed tomography device 1.

The imaging apparatus 2 comprises a gantry 20, the acquisition region 4, the patient support apparatus 10, a projection data acquisition apparatus 26, 28 and a control apparatus 30. The gantry 20 comprises a stationary support mass 21 and a rotor 24. The rotor 24 is rotatably mounted about an axis of rotation via a rotational support apparatus. The acquisition region 4 is formed by a tunnel-shaped opening in the gantry 20. A region of an object, in particular the patient 13, to be depicted can be arranged in the acquisition region 4.

The projection data acquisition apparatus 26, 28 comprises a radiation source 26, for example an X-ray source, and a detector 28, for example an X-ray detector. The radiation source 26 is arranged on the rotor 24 and embodied for the emission of radiation, for example X-rays, with radiation quanta 27. The detector 28 is arranged on the rotor 24 and embodied to detect the radiation quanta 27. The radiation quanta 27 can travel from the radiation source 26 to the region to be depicted and, following interaction with the region to be depicted, arrive at the detector 28. This enables the acquisition of projection data of the region to be depicted. The projection data acquired by the projection data acquisition apparatus 26, 28 is forwarded to the control apparatus 30. The control apparatus 30 is a computer, in particular a digital computer, and embodied to control the imaging apparatus 2. The control apparatus comprises an image reconstruction device 34. The image reconstruction device 34 can reconstruct an image on the basis of the projection data.

The imaging apparatus 2 comprises an input apparatus 38 and an output apparatus 39. The input apparatus 38 is embodied to input control information, for example image reconstruction parameters and/or examination parameters. The output apparatus 39 is embodied to output control information and/or images.

The arrangement according to the seventh embodiment of the invention comprises the arrangement according to the sixth embodiment of the invention. The seventh embodiment of the invention provides that the bioelectric signal is acquired via the differential voltage system DS and forwarded to the control apparatus 30. The bioelectric signal can be further processed by way of the control apparatus 30. In particular the imaging apparatus 2, in particular the projection data acquisition apparatus 26, 28 and/or the image reconstruction device 34 can be controlled on the basis of the bioelectric signal. For example, the bioelectric signal can trigger the acquisition of projection data and/or effect the selection of projection data for a reconstruction of an image.

The seventh embodiment of the invention provides that the first layer L1 forms a non-conductive recess 18 and that the recess 18 extends in a longitudinal direction of the overlay 15. The seventh embodiment of the invention provides that the first measuring path M1 comprises a first electric line W1 and the second measuring path M2 comprises a second electric line W2, wherein the first line W1 and the second line W2 on the overlay 15 are arranged or can be arranged in the region 19 defined by the recess 18. This enables the parasitic capacitance CEKG to be further reduced. Thus, the invention facilitates an efficient reduction in the partial current IEKG and hence improved suppression of the common-mode interference signal.

BIBLIOGRAPHY

[BC11]
Bill Crone: "Improving Common-mode Rejection Using the Right-Leg Drive Amplifier". Analog Devices, Technical Article. MS-2125, January 2011. http://www.analog.com/static/imported-files/tech_articles/MS-2125.pdf The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An arrangement, comprising:
   a patient support apparatus including a support plate and an overlay for the support plate, the support plate or the overlay including an electrically conductive first layer, wherein the electrically conductive first layer is connected or configured to be connected to a contact-making apparatus via a first electric transmission path, wherein the contact-making apparatus is connected or configured to be connected to at least one of ground and a mass, via a second electric transmission path, wherein, in an operating mode of the arrangement, in which a patient is supported on the patient support apparatus, the electrically conductive first layer is connected or configured to be connected to the patient, via a third electric transmission path, wherein the support plate or the overlay includes an electrically non-conductive second layer, wherein the electrically non-conductive second layer forms a capacitive coupling section of the third transmission path, wherein the support plate includes an electrically conductive third layer, wherein the contact-making apparatus includes the electrically conductive third layer, wherein the support plate includes an electrically non-conductive fourth layer, and wherein the electrically non-conductive fourth layer forms a capacitive coupling section of the first transmission path.

2. The arrangement of claim 1, wherein the overlay includes an at least one of an overlay core region and an overlay edge region and wherein at least one of the overlay core region includes the electrically conductive first layer and the overlay edge region includes the electrically non-conductive second layer.

3. The arrangement of claim 2, wherein the electrically conductive first layer forms a non-conductive recess, and wherein one or more electric lines are arranged or configured to be arranged on the overlay in a region defined by the recess.

4. The arrangement of claim 2, wherein the contact-making apparatus comprises a first connection partner of a detachable electric connection, and wherein the second transmission path comprises a second connection partner of the detachable electric connection corresponding to the first connection partner.

5. The arrangement of claim 2, wherein at least one of the support plate and the overlay is transparent to X-rays from an X-ray source in a medical imaging apparatus.

6. The arrangement of claim 1, wherein the electrically conductive first layer forms a non-conductive recess, and wherein one or more electric lines are arranged or configured to be arranged on the overlay in a region defined by the recess.

7. The arrangement of claim 6, wherein the recess extends in a longitudinal direction of the overlay.

8. The arrangement of claim 6, further comprising a differential voltage measuring system to measure a bioelectric signal, wherein, in the operating mode of the arrangement in which the patient is supported on the patient support apparatus, a first electric measuring path of the differential voltage measuring system and a second electric measuring path of the differential voltage measuring system are connected or configured to be connected to the patient.

9. The arrangement of claim 8, wherein the first measuring path includes a first electric line and the second measuring path includes a second electric line, and wherein at least one of the first line and the second line are arranged or configured to be arranged on the overlay in the region defined by the recess.

10. The arrangement of claim 1, wherein the contact-making apparatus includes a first connection partner of a detachable electric connection, and wherein the second transmission path includes a second connection partner of the detachable electric connection corresponding to the first connection partner.

11. The arrangement of claim 1, wherein the support plate includes at least one of a support plate core region and a support plate edge region,
and wherein at least one of
the support plate core region includes at least one of the electrically conductive first layer and the electrically conductive third layer, and
the support plate edge region includes at least one of the electrically non-conductive second layer and the electrically non-conductive fourth layer.

12. The arrangement of claim 1,
wherein at least one of
surface resistivity of the electrically conductive first layer is at least one of greater than 100 ohm and lower than 1 mega-ohm, and
surface resistivity of the electrically conductive third layer is at least one of greater than 100 ohm and lower than 1 mega-ohm,
and wherein at least one of
surface resistivity of the electrically non-conductive second layer is at least one of greater than 1 mega-ohm and lower than 1 giga-ohm, and
surface resistivity of the electrically non-conductive fourth layer is at least one of greater than 1 mega-ohm and lower than 1 giga-ohm.

13. The arrangement of claim 1, wherein at least one of
relative permittivity of the electrically non-conductive second layer is greater than 5 and
relative permittivity of the electrically non-conductive fourth layer is greater than 5.

14. The arrangement of claim 1, wherein at least one of the first transmission path, the second transmission path, the third transmission path and combinations of at least two of the first transmission path, the second transmission path, and the third transmission path includes a capacitive component at least one of greater than 100 pico-farad and lower than 100 nano-farad.

15. The arrangement of claim 1, wherein at least one of the support plate and the overlay is transparent to X-rays from an X-ray source in a medical imaging apparatus.

16. The arrangement of claim 1, wherein at least one of the support plate and the overlay includes a region made of at least one of
one or more plastics, one or more carbon-containing and carbon-fiber-reinforced materials,
and wherein the region includes a layer selected from the group consisting of the electrically conductive first layer, the electrically non-conductive second layer, the electrically conductive third layer and the electrically non-conductive fourth layer.

17. The arrangement of claim 1, wherein at least one of the electrically conductive first layer and the electrically conductive third layer is selected from the group consisting of a conductive plastic layer, a conductive plastic foam layer, a conductive plastic film, a conductive textile layer, a conductive fabric layer and combinations thereof.

18. The arrangement of claim 1, further comprising:
an imaging apparatus including an acquisition region formed by a tunnel-shaped opening, wherein the patient support apparatus comprises a support table and wherein the support plate is arranged movably on the support table relative to the support table such that the support plate is introduceable into acquisition region in a longitudinal direction of the support plate.

19. The arrangement of claim 1, wherein on a contact surface selected from the contact surface group consisting of a common contact surface of the support plate and the overlay, a common contact surface of the support plate and the support table and a common contact surface of the overlay and the support table, the contact partners of the contact surface are similar or the same with respect to a property, wherein the property is selected from the property group consisting of material, electron affinity, electron work function, triboelectric charging behavior, position in the triboelectric series, surface resistance and combinations thereof.

20. The arrangement of claim 1, wherein the support plate includes an electrically conductive additional layer, and wherein the contact-making apparatus includes the additional layer.

21. The arrangement of claim 1, wherein the support plate includes an electrically non-conductive additional layer, and wherein the additional layer forms a capacitive coupling section of the first transmission path.

22. The arrangement of claim 1, wherein the support plate includes at least one of a support plate core region and a support plate edge region,
and wherein at least one of
the support plate core region includes the electrically conductive first layer, and
the support plate edge region includes the electrically non-conductive second layer.

23. The arrangement of claim 1,
wherein at least one of
the surface resistivity of the electrically conductive first layer is at least one of greater than 100 Ohm and lower than 1 mega-ohm, and
the surface resistivity of the electrically non-conductive second layer is at least one of greater than 1 mega-ohm and lower than 1 giga-ohm.

24. The arrangement of claim 1, wherein the relative permittivity of the electrically non-conductive second layer is greater than 5.

25. The arrangement of claim 1, wherein at least one of the support plate and the overlay includes a region made of at least one of
one or more plastics, one or more carbon-containing and carbon-fiber-reinforced materials,
and wherein the region includes a layer selected from the group consisting of the electrically conductive first layer and the electrically non-conductive second layer.

26. The arrangement of claim 1, wherein the electrically conductive first layer is selected from the group consisting of a conductive plastic layer, a conductive plastic foam layer, a conductive plastic film, a conductive textile layer, a conductive fabric layer and combinations thereof.

27. The arrangement of claim 1, further comprising
a differential voltage measuring system to measure a bioelectric signal, wherein, in the operating mode of the arrangement in which the patient is supported on the patient support apparatus, a first electric measuring path of the differential voltage measuring system and a second electric measuring path of the differential voltage measuring system are connected or configured to be connected to the patient.

* * * * *